United States Patent [19]

Salaita

[11] Patent Number: 4,645,935
[45] Date of Patent: Feb. 24, 1987

[54] METHOD AND APPARATUS FOR MEASURING THERMAL NEUTRON ABSORPTION CROSS-SECTION

[75] Inventor: George N. Salaita, Anaheim, Calif.

[73] Assignee: Chevron Research Company, San Francisco, Calif.

[21] Appl. No.: 672,427

[22] Filed: Oct. 31, 1984

[51] Int. Cl.[4] .................. G01N 23/09; G01N 23/10
[52] U.S. Cl. .................. 250/390; 250/391; 250/255
[58] Field of Search .......... 250/390 E, 390 D, 390 C, 250/391, 255, 357.1

[56] References Cited

FOREIGN PATENT DOCUMENTS 2053064 5/1971 Fed. Rep. of Germany ... 250/390 C

OTHER PUBLICATIONS

Enrico Fermi and Leo Szilard, "Method for Testing Materials", published abstract of Patent Application Ser. No. 534,681, *Official Gazette*, vol. 667 (Feb. 1953), p. 762.
"Measurement of the Thermal Neutron Absorption Cross Section of Rock Samples by a Pulsed Source Method", by L. S. Allen and W. R. Mills, Jr.—15th Annual SPWLA Symposium Proceedings Paper, Jun. 2-5, 1974, pp. 289-295.
"Measuring the Thermal Neutron Absorption Cross Sections of Rocks", by C. W. Tittle and G. W. Crawford, *The Log Analyst*, May-Jun. 1983, pp. 12-15.
"Measuring the Neutron Cross Section of Rocks", by C. W. Tittle and G. W. Crawford—SPWLA 25th Annual Logging Symposium, Jun. 10-13, 1984.
"A System for Wellsite Measurement of Fluid", by J. W. Hall, J. Tittman, and H. N. Edmundson, SPWLA 21st Annual Logging Symposium, Jul. 8-11, 1980, pp. 1-8.
"Measuring Thermal Neutron Absorption Cross Sections of Formation Brines", by C. E. Rinehart and H. J. Weber—16th Annual SPWLA Logging Symposium, Jun. 1975, pp. 297-310.
"Measurement of the Thermal Neutron Absorption Cross Section of Rock Samples", by J. A. Czubek, K. Drozdowicz, E. Krynick-a-Drozdowicz, A. Igielski and U. Woznicka, *Int. J. Appl. Radiat. Isot.*, vol. 34, pp. 143-151 (1983).
"A Simple and Rapid Method of Determining the Thermal Neutron Absorption Cross Section of Rocks", by A. Dydejczyk, J. Gyurcsak and A. Kreft, *Proceedings of the IAEA Consultants' Meeting on Nuclear Data for Bore-Hole and Bulk-Media Assay Using Nuclear Techniques*, Krakow, Poland (Nov. 1983), pp. 313-317.

*Primary Examiner*—Janice A. Howell
*Assistant Examiner*—Constantine Hannaher
*Attorney, Agent, or Firm*—S. R. LaPaglia; E. J. Keeling; H. D. Messner

[57] ABSTRACT

The thermal neutron absorption cross-section of a sample is measured by placing the sample in a sample container which surrounds a cavity within which a neutron source is positioned. A detector is positioned along a line parallel to an axis passing through the cavity. The source and detector are immersed in a moderator within a tank.

18 Claims, 3 Drawing Figures

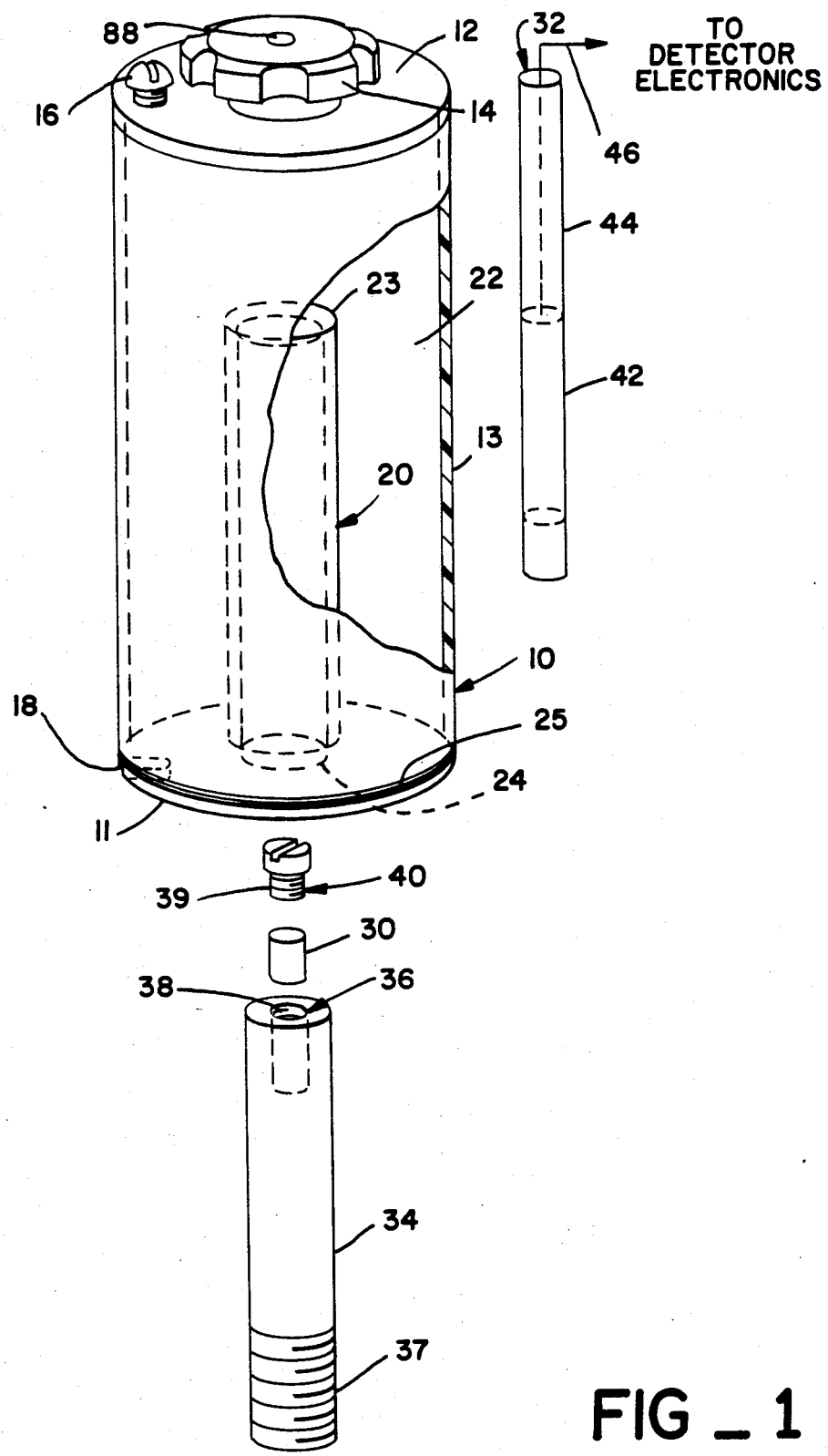
FIG_1

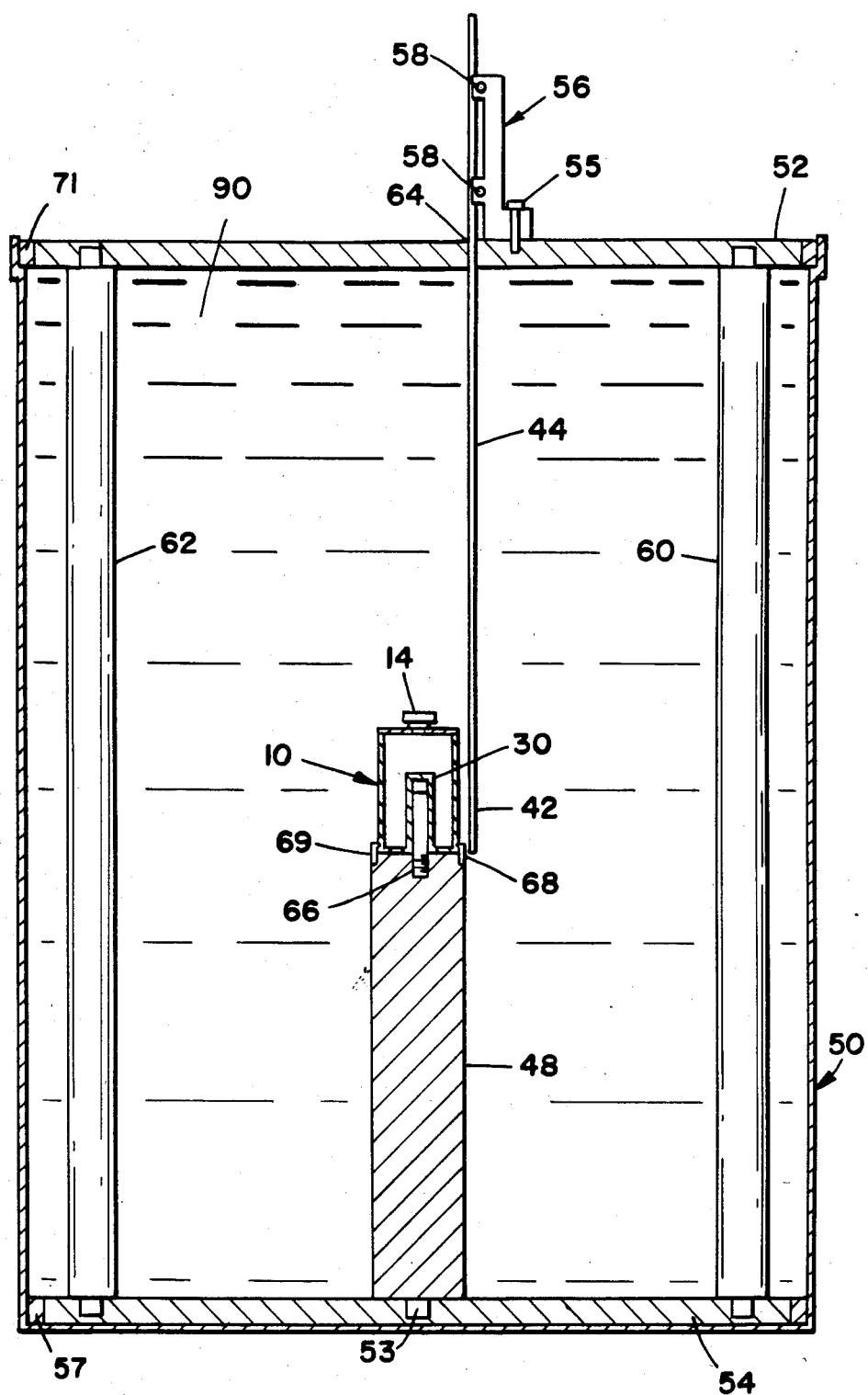
FIG_2

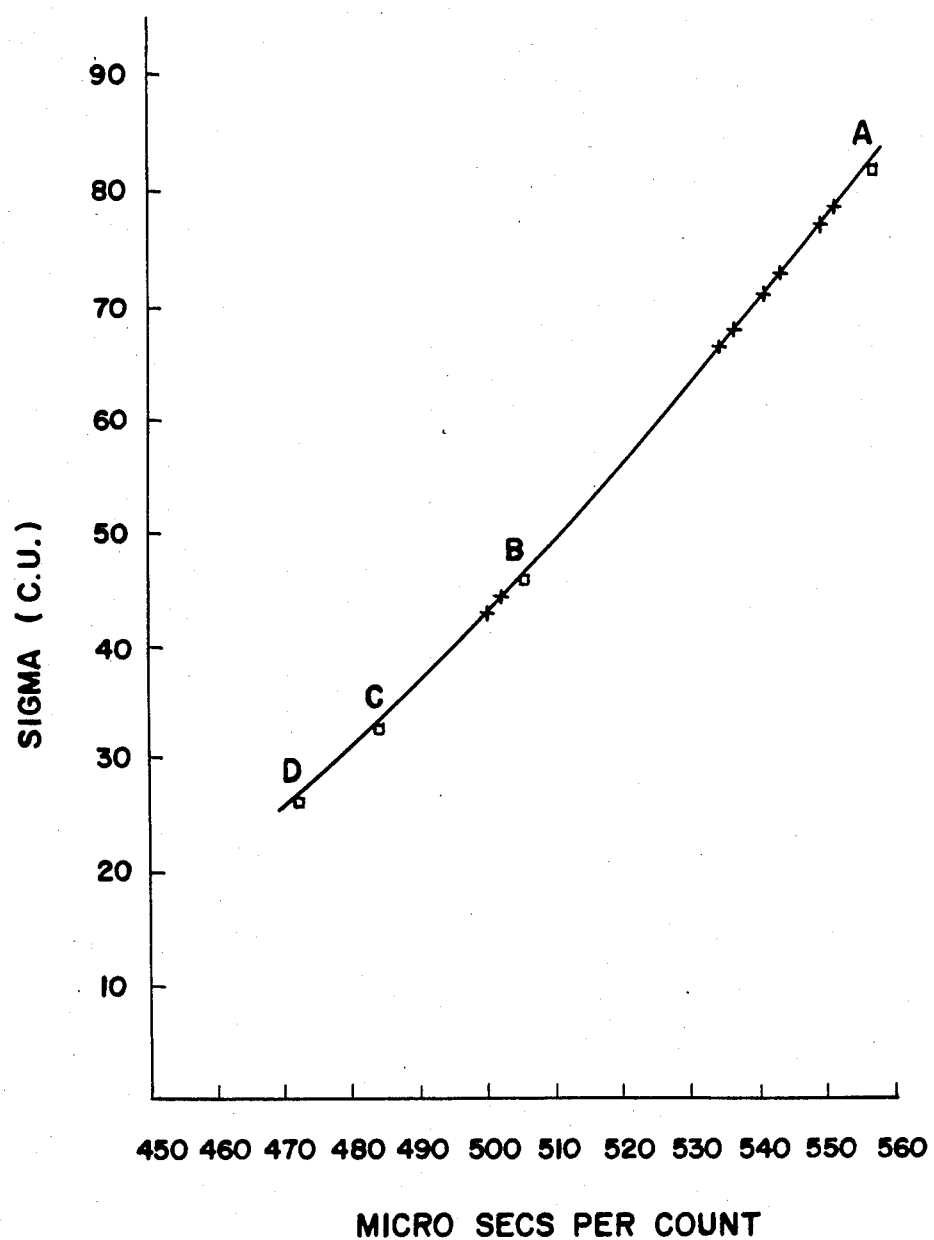
FIG_3

METHOD AND APPARATUS FOR MEASURING THERMAL NEUTRON ABSORPTION CROSS-SECTION

BACKGROUND OF THE INVENTION

The present invention pertains in general to methods and apparatus for measuring properties of samples exposed to radioactive sources and in particular to methods and apparatus for measuring the thermal neutron absorption cross-section for rock and fluid formation samples.

Pulsed-neutron logging is one of the well-logging techniques applied in order to provide information relating to the content of hydrocarbons in subsurface geological formations. Pulsed-neutron techniques are commonly used to determine the neutron life time of a formation such that $$\tau = 1/(v\Sigma_a) \tag{1}$$

where:
- $\tau$ = the neutron life time of the formation;
- $v$ = the thermal neutron velocity in the formation; and
- $\Sigma_a$ = the absorption cross-section of thermal neutrons in the formation.

As can be seen from Equation (1), the thermal neutron absorption cross-section of formation materials may be deduced, assuming that the thermal neutron velocity $v$ is known. However, the thermal neutron absorption cross-section of the formation $\Sigma_a$ does not by itself provide an indication of hydrocarbon composition because it is a linear combination of the thermal neutron absorption cross-sections of all rock components. For example, in a particular well, $$\Sigma_a = (1 - \phi - V_{sh})\Sigma_r + V_{sh}\Sigma_{sh} + \phi(1-S_w)\Sigma_h + \phi S_w \Sigma_w \tag{2}$$

where:
- $\phi$ = the porosity of the formation;
- $V_{sh}$ = the shale content of the formation;
- $\Sigma_r$ = the absorption cross-section of the formation's rock matrix;
- $\Sigma_{sh}$ = the absorption cross-section of the shale in the formation;
- $\Sigma_h$ = the absorption cross-section of formation hydrocarbons;
- $\Sigma_w$ = the absorption cross-section of formation water; and where
- $\Sigma_a$ is as defined above.

Consequently, it is useful to be able to determine the thermal neutron absorption cross-sections of samples of formation materials in order to be better able to interpret the results of pulsed neutron well logging.

Most methods for measuring thermal neutron absorption cross-sections have required the use of samples which are relatively large in mass or volume. Methods which permit relatively small sample sizes tend to have relatively large errors.

Some techniques have been useful only with fluids, while others have been useful only for rock samples. Some of the techniques which apply to formation fluids, require dilution of those fluids to make up a required volume of up to one gallon.

Measurements of thermal neutron absorption cross-section are obtained from pulsed neutron die-away measurement or steady-state thermal neutron flux measurements. Existing approaches employing die-away measurements rely upon reactors and accelerators as sources of neutrons. Because such techniques require the use of complicated and costly equipment, they tend to be done at central locations far from the source of the material and are both costly and time consuming to obtain. Flux measurements are made using steady-state sources which are simple and inexpensive to use. However, the relative positions of the neutron source, the sample and the detector, are very important in determining the sensitivity of a flux measurement.

Because accelerators and reactors are large pieces of equipment, they do not readily provide small neutron sources capable of placement within a sample. Consequently, the source is positioned at some distance away from the sample. A detector which is particularly sensitive to thermal as oppossed to fast neutrons, is placed within the sample or around the periphery of the sample but not between the sample and source. Losses due to scattering of neutrons create problems of calculation and interpretation.

Although thermal neutron flux measurement may be made by using the same configurations of sample, source and detector required by pulsed neutrons measurements, a small source and the reduced degree of scattering allow different configurations to be implemented. Specifically, the source has been mounted parallel to or concentrically on the detector within a fluid sample in the absence of a moderator. However, such techniques have required dilution up to a volume of one gallon, making them impractical for small samples in general, and solid samples in particular.

SUMMARY OF THE INVENTION

Accordingly, an apparatus according to the present invention measures the thermal neutron absorption cross-section of a sample. In the apparatus, the sample container has an axis and has an outer surface defining an inner cavity. Along the axis, the outer surface has a pocket, protruding into the inner cavity, within which pocket is located means for positioning a source of thermal neutrons. A detector of thermal neutrons is positioned along a line parallel to the axis but outside of either the inner cavity or the pocket.

The present invention also provides a method of measuring the thermal neutron aborption cross-section of a sample. The method involves placing a neutron source within the sample, positioning a detector outside of the sample, and counting thermal neutrons impinging on the detector.

BRIEF DESCRIPTION OF THE DRAWINGS

FIG. 1 is a view in perspective of a sample container, source and detector according to the preferred embodiment of the present invention, which view is cut away to show internal components of the sample container;

FIG. 2 is a view in partial cross-section of the embodiment of FIG. 1 positioned within a tank according to the present invention; and FIG. 3 is a calibration curve obtained by measurements within the embodiment of FIGS. 1 and 2.

DESCRIPTION OF THE PREFERRED EMBODIMENT

In a preferred embodiment of the present invention, as illustrated in FIG. 1, a cylindrical sample container 10 as a circular bottom 11, a circular top 12, and a sidewall 13. A central threaded aperture (not shown) in top 12 is threadedly engaged with a fill cap 14. Similarly, a peripheral threaded aperture (not shown) in top 12 is threadedly engaged with a slotted pressure relief cap 16. A positioning slot 18 extends from the edge of bottom 11 toward the center of bottom 11. A V-shaped, circular groove 25 extends around the circumference of sample container 10 parallel with bottom 11.

A cylindrical pocket 20 of bottom 11 extends through bottom 11 into an internal cavity 22 formed by sidewall 13. Pocket 20 is coaxial with sample container 10. Pocket 20 has a closed end 23 within cavity 22 and has an open end 24 at bottom 11.

A source of neutrons 30 fits within a cavity 36 of a cylindrical positioning peg 34. Cavity 36 has a threaded aperture 38 which is threadedly engageable with threaded end 39 of a slotted plug 40. Peg 34 has an externally threaded end 37.

A neutron detector element 42 is coaxially connected with a hollow extension rod 44. Through a central cavity 32 of rod 44 an electrical conductor 46 is passed.

Turning now to FIG. 2 in which the structures also shown in FIG. 1 are identified by the same reference numerals used to identify them therein, sample container 10 is placed atop a post 48 in the center of a cylindrical tank 50 which has a curved side wall and a bottom. Post 48 has a threaded projection 53 which is threadedly engaged with a threaded cavity in a circular bottom plate 54. Hollow rod 44 passes through an aperture 64 in top plate 52. Detector 42 is attached to an end of rod 44 proximal to and parallel to the axis of sample container 10. A circular top plate 52 is parallel to bottom plate 54. Top plate 52 and bottom plate 54 are rigidly cnnected parallel to each other four cylindrical posts, two of which, 60 and 62, are shown in FIG. 2. Each of these posts is threadedly engaged with top plate 52 at a first end and with bottom plate 54 at a second end. Bottom plate 54 is separated from the internal surface of tank 50 by a first positioning doughnut 57. Top plate 52 is separated from the lip of tank 50 by a second positioning doughnut 71. A bolt 55 is tightened into a threaded aperture of top plate 52 after passing through a first portion of a detector support jig 56. A second portion of jig 56, perpendicular to the first portion, has clamps 58 which grip rod 44.

As is clear to one skilled in the art, the rigid connection of the top and bottom plates with the detector and sample container allows detector, sample and source to be assembled in a chosen, reproducible configuration and allows that configuration to be maintained during and after placement within tank 50. Doughnuts 57 and 71 further aid in assuring that a desired placement of sample, source and detector is effected within tank 50.

A second detector, similar to detector 42, may be similarly positioned parallel to the axis of sample container 10 for use as a monitor and a back-up. Such a second detector may be conveniently positioned at 90° or 180° to detector 42 about the circumference of container 10, for example. Doughnuts 57 and 71 further aid in assuring that a desired placement of sample, source and detector is effected within tank 50.

An upper end of post 48 has a threaded cavity 66 threadedly engaged with end 37 of peg 34. Post 48 also has right angled strips 68 and 69 which engage groove 25 on sample container 10 and is positioning ridge (not shown) which engages positioning slot 18 in sample container 10. All of these structures promote reproducible placement.

Source 30 may be any source of thermal neutrons but is preferably a pellet of $^{252}$Cf. Detector 42 may be a He$^3$ proportional counter having a $\frac{1}{4}"\times 2"$ active volume and being 5/16" in outer diameter available from the Reuter-Stokers Company, Cleveland, Ohio. Cap 14, plugs 16 and 40, container 10, peg 34, post 48, and posts 60 and 62, may be readily manufactured on commonly available acrylic materials or purchased from a number of sources usually accessible by one skilled in the art. Polyethylene tanks suitable for use as tank 50 are also readily available.

As shown in FIG. 2, when asembled, peg 34, containing source 30 within cavity 32, is positioned within pocket 20. The fit between pocket 20 and peg 34 should be the tightest consistent with convenient removal in order to promote reproducibility of positioning.

In fact, an important advantage of the present invention is that the sample, source and detector are held in reproducible positions so that human affects on positioning are eliminated. This end is also served by the engagement of slot 18 with a projection of post 48 and by the engagement of groove 25 with strips 68 and 69 in order to control, axial rotation and vertical movement of sample container 10.

Detector 42 may also be a BF$_3$ detector, a small fission chamber, a scintillation detector, a lithium glass detector or any other suitable detector of thermal neutrons. Source 30 may be a Am-Be pellet.

In order to use the apparatus of FIGS. 1 and 2, a sample is introduced into sample container 10 through the threaded aperture in top 12, cap 14 is tightened in place and bubbles are removed through the peripheral aperture in top 12 before tightening plug 16 into place.

Source 30 is placed within peg 34 and plug 40 is tightened into place above source 30. Peg 34 is threadedly engaged with post 48. Sample container 10 is engaged by strips 69 and 68 and the whole assembly is placed in the center of tank 50 within a moderating medium of distilled, deionized water which normally fills tank 50. Final positioning of container 10 may be accomplished by engaging a threaded depression 88 (shown in FIG. 1) with a threaded end of a rod (not shown) passed through an aperture (not shown) in top plate 52. When conductor 46 is connected to appropriate detector electronic equipment, measurement of thermal neutron absorption cross-section via neutron counting may begin.

The linear dimensions of tank 50 are selected to be on the order of several diffusion lengths of thermal neutrons produced by source 30. The diameter of sample container 10 is selected to be approximately equal to the neutron slowing-down length in liquid samples.

Signals from detector 42 pass along conductor 46 to a counter where they are amplified and shaped in a preamplifier (not shown) and amplified in an amplifier (not shown). A single-channel-analyzer window is at the amplifier output to count primarily thermal neutron absorption events on a timer/scaler.

Moderator 90 in tank 50 moderates fast neutrons to thermal energy levels. On the average, at a given point in the tank, the rate of neutron absorption equals the numbers of neutrons produced per second. When a sample is introduced into the tank, it depresses the neutron flux and, consequently, the neutron count rate in a manner that is related to the absorption cross-section of the sample $\Sigma$. Assuming that the strength of the source remains constant, the steady state neutrons flux measured by detector 42 is proportional to $1/\Sigma$.

For an infinite medium, that is, one for which there is practically no leakage of neutrons, the number of neutrons absorbed per second at a distance r from a source is equal to the number emitted by the source per second.

A neutron detector placed near the absorber measures the change in the neutron flux count rate C. The neutron observed by a neutron detector is related to the neutron absorber cross-section by the relation $$\Sigma_{ab} = b/C \qquad (3)$$

where:
C = The count rate observed by a neutron detector;
$\Sigma_{ab}$ = the neutron absorber cross-section; and
b = a constant that invlves source strength and an instrument proportionality constant.

Thus, the plot of $\Sigma_{ab}$ versus 1/C (or $\Sigma_{ab}$ versus C) should approximate a straight line.

In practice, the apparatus according to the present invention is calibrated for measuring the absorption cross-section of either fluid or rock samples as follows:

For Fluid Samples

1. Fill sample containers with solutions of distilled water and pure NaCl and of water poisoned with boron of gradually increasing concentrations.
2. For each NaCl or boron solution, place the container in place and measure the count rate of the 3 He counter. [Steps 1 and 2 establish a calibration curve from the plot of $\Sigma_{solution}$ (as calculated from the mixture) vs. count rate (or reciprocal count rate) and are use to derive a least squares fit curve by well-understood techniques.]
3. Fill the sample container with the fluid to be measured.
4. Find $\Sigma$ for the unknown from the count rate and the least squares fit curve.

For Rock Samples

A set of standard or reference rock samples of known thermal neutron absorption cross-sections are prepared as follows:

1. Saturate a set of samples with fresh water and with boric acid solutions (or standard brines) of gradually increasing cross-sections.
2. Perform Steps 1 and 2 above for fluid samples.
3. Saturate the unknown rock sample with fresh water and measure as in Step 3.
4. From the count rate, the least square fit curve and the measured porosity, calculate the cross-section of the unknown rock sample.

Steps 1 through 4 should be repeated for each rock type, for example, sandstone, limestone and dolomite. Rock samples of unknown cross-sections are usually measured against similar rock calibration standards.

Properties of standard brines for calibration of the apparatus according to the present invention, are exemplified in Table I.

TABLE I

| Brine | Resistivity at 25° C. Ωm | M moles 1000 gm H$_2$O | gm NaCl 1000 gm H$_2$O | PPM NaCl | Density gm/cc | NMR Ti Sec |
|---|---|---|---|---|---|---|
| A | 0.05000 | 3.2917 | 192.37 | 161.334 | 1.1143 | 2.99 |
| B | 0.1000 | 1.2325 | 72.031 | 67.191 | 1.0446 | 2.99 |
| C | 0.2000 | 0.5454 | 31.875 | 30.890 | 1.0187 | 2.95 |
| D | 0.5000 | 0.1977 | 11.554 | 11.422 | 1.0051 | 2.95 |

FIG. 3 illustrates a calibration curve for well log lab brines W, X, Y and Z as compared to counts obtained from the brines of Table I as illustrated in TABLE II.

For the measurements illustrated in Table II and in FIG. 3, each count rate, or reciprocal, represents an average of fifteen 200-second runs. The macroscopic thermal neutron absorption cross-section for each sample is derived from a least squares fit of standard samples.

TABLE II

| Sample | Mean Counts | Standard Deviation | Standard Error | Micro Secs Per Count | Sigma (C.U.) | Specific Gravity | Equiv. Salinity (KPPM) |
|---|---|---|---|---|---|---|---|
| D Brine | 424491.04 | 480.84 | 124.15 | 471.15 | 26.020 | 1.0051 | 11.42 |
| C Brine | 414832.96 | 577.24 | 182.54 | 482.12 | 32.710 | 1.0187 | 30.89 |
| B Brine | 396735.52 | 578.15 | 182.83 | 504.11 | 45.670 | 1.0446 | 67.19 |
| A brine | 360112.00 | 614.00 | 194.16 | 555.38 | 82.270 | 1.1143 | 161.33 |
| Well Log Lab Brines | | | | | | | |
| W | 400089.44 | 455.30 | 117.56 | 499.89 | 43.137 | 1.043 | 59.86 |
| W | 399028.80 | 554.48 | 127.21 | 501.22 | 43.975 | 1.043 | 62.37 |
| X | 363597.28 | 550.19 | 142.06 | 550.06 | 78.134 | 1.108 | 150.88 |
| X | 364644.48 | 726.15 | 194.07 | 548.48 | 76.927 | 1.108 | 147.47 |
| Y | 373391.68 | 567.27 | 146.47 | 535.63 | 67.362 | 1.082 | 125.15 |
| Y | 374661.44 | 814.98 | 197.66 | 533.81 | 66.047 | 1.082 | 121.35 |
| Z | 370287.36 | 285.49 | 116.55 | 540.12 | 70.653 | 1.092 | 132.84 |
| Z | 368743.68 | 722.36 | 186.51 | 542.38 | 72.331 | 1.092 | 137.65 |

While the present invention has been described in terms of a preferred embodiment, further modifications and improvements will occur to those skilled in the art. For example, with some modification, the apparatus and method according to the present invention may be used for measuring the diffusion length of mixed media (e.g., liquid and rock samples). I desire it to be understood, therefore, that this invention is not limited to the particular form shown that I intend in the appended claims to cover all sorts of equivalent variations which come within the scope of the invention as claimed.

What is claimed is:
1. Apparatus for measuring the thermal neutron absorption cross-section of a geologic sample comprising:
   a means for holding a geologic sample having an axis, having an outer surface defining an inner cavity, said outer surface having a pocket protruding into said inner cavity along said axis;

means for positioning a source of thermal neutrons within said pocket; and a thermal neutron detector positioned along a line parallel to said axis outside of said cavity and outside of said pocket;

a water tank surrounding said means for holding a geologic sample, said means for positioning, and said detector.

2. The apparatus as recited in claim 1 wherein said axis is an axis of symmetry.

3. The apparatus as recited in claim 2 wherein said means for holding a geologic sample is cylindrical in shape, said axis is axis of rotation of said cylinder, said pocket is cylindrical in shape and wherein said pocket is coaxial with said means for holding a geologic sample.

4. The apparatus as recited in claim 3 wherein said tank is cylindrical.

5. The apparatus as recited in claim 4 wherein said tank is coaxial with said means for holding a geologic sample.

6. The apparatus as recited in claim 5 further comprising means for positioning said means for holding a geologic sample in said tank.

7. The apparatus as recited in claim 6 wherein said means for holding a geologic means for positioning said sample comprises a port within said tank.

8. The apparatus as recited in claim 7 further comprising a source of thermal neutrons positioned within said pocket by said means for positioning.

9. A method of measuring the thermal neutron absorption cross-section of a geologic sample comprising the steps of:

placing a neutron source within the geologic sample;

positioning a detector outside of the sample and orienting said detector so that the only direct path between the source and the detector is through the sample, placing water around said sample and said detector, and;

counting thermal neutrons impinging on the detector.

10. Apparatus for measuring the thermal neutron absorption cross-section of a liquid sample comprising:

means for holding a liquid sample having an axis, having an outer surface defining an inner cavity, said outer surface having a pocket protruding into said inner cavity along said axis;

means for positioning a source of thermal neutrons within said pocket; and a thermal neutron detector poitioned along a line parallel to said axis outside of said cavity and outside of said pocket;

a water tank surrounding said means for holding a liquid, sample, said means for positioning, and said detector.

11. The apparatus as recited in claim 10 wherein said axis is an axis of symmetry.

12. The apparatus as recited in claim 11 wherein said means for holding a liquid sample is cylindrical in shape, said axis is an axis of rotation of said cylinder, said pocket is cylindrical in shape, and said pocket is coaxial with said means for holding a liquid 13. The apparatus as recited in claim 12 wherein said tank is cylindrical.

14. The apparatus as recited in claim 13 wherein said tank is coaxial with said means for holding a liquid sample.

15. The apparatus as recited in claim 14 further comprising means for positioning said means for holding a liquid.

16. The apparatus as recited in claim 15 wherein said means for positioning comprises a post within said tank.

17. The apparatus as recited in claim 16 further comprising a source of thermal neutrons positioned within said pocket by said means for positioning.

18. A method of measuring the thermal neutron absorption cross-section of a liquid sample comprising the steps of:

placing a neutron source within the liquid sample;

positioning a detector outside of the sample;

placing water around said sample and said detector;

orienting said detector so that the only direct path between the source and the detector is through the sample; and counting thermal neutrons impinging on the detector.

* * * * *